United States Patent
Hara et al.

(10) Patent No.: US 6,407,087 B1
(45) Date of Patent: Jun. 18, 2002

(54) UCF116 DERIVATIVES

(75) Inventors: Mitsunobu Hara, Shunto-gun; Shiro Akinaga, Shizuoka; Yutaka Kanda, Machida, all of (JP); Timothy S. Powers, San Francisco, CA (US); David A. Johnson, West Carmel, IN (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/605,014

(22) Filed: Jun. 27, 2000

Related U.S. Application Data

(60) Provisional application No. 60/140,838, filed on Jun. 28, 1999.

(51) Int. Cl.[7] .................... C07D 225/06; A61K 31/395
(52) U.S. Cl. ........................ 514/183; 540/520
(58) Field of Search ..................... 540/520; 514/183

(56) References Cited

U.S. PATENT DOCUMENTS 4,587,237 A  5/1986  Otake et al. ............... 514/183

FOREIGN PATENT DOCUMENTS

EP  07398833 A  10/1996

*Primary Examiner*—Bruck Kifle
(74) *Attorney, Agent, or Firm*—Fitzpatrick, Cella, Harper & Scinto

(57) ABSTRACT

UCF116 derivatives represented by formula (I):

wherein

Q represents and R represents hydrogen, $C(=O)R^{1a}$ (wherein $R^{1a}$ represents methyl, ethyl, propyl, isopropyl, 2,2-dimethylpropyl, pentyl, alkyl having 6 to 10 carbon atoms, 1-propenyl, isopropenyl, 2-methyl-1-propenyl, substituted or unsubstituted alicyclic alkyl having 3 to 5 carbon atoms, substituted or unsubstituted aryl, substituted or unsubstituted aralkyl, a substituted or unsubstituted heterocyclic group, substituted or unsubstituted aralkyloxy, or substituted lower alkyl), $C(=X)NHR^{1b}$ (wherein X represents an oxygen or sulfur atom, and $R^{1b}$ represents substituted or unsubstituted lower alkyl, substituted or unsubstituted alicyclic alkyl, substituted or unsubstituted lower alkoxycarbonyl, substituted or unsubstituted aryl, substituted or unsubstituted aralkyl, or a substituted or unsubstituted heterocyclic group), or $SO_2R^{1c}$ (wherein $R^{1c}$ represents substituted or unsubstituted lower alkyl, substituted or unsubstituted aryl, substituted or unsubstituted aralkyl, a substituted or unsubstituted heterocyclic group, or substituted or unsubstituted lower alkenyl), with the proviso that, when Q is R is not benzoyl; salts thereof; isomers thereof; hydrates thereof; or solvates thereof.

12 Claims, No Drawings

UCF116 DERIVATIVES

This Application claims benefit of U.S. Provisional No. 60/140,838 filed Jun. 28, 1999.

TECHNICAL FIELD

The present invention relates to novel UCF116 derivatives or salts thereof which have antitumor and antibacterial activities and are useful as antitumor agents. Also, the present invention relates to a pharmaceutical composition which comprises the UCF116 derivative or a pharmaceutically acceptable salt thereof and a pharmaceutically acceptable carrier.

BACKGROUND ART

Compounds which are represented by the following structural formulae, namely UCF116-B and UCF116-D (WO 96/15114), mycotrienin II and mycotrienin I [*Journal of Antibiotics*, 35:1460, 1467, 1474 (1982), *Tetrahedron Letters*, 32:841 (1991)], T-23-VIII and T-23-IX (U.S. Pat. No. 4,587,237), ansatrienin A2 and ansatrienin A3 [*Journal of Antibiotics*, 36:187 (1983)], ansatrienin A4 [*Journal of Natural Products*, 50:108 (1987)] and hexadehydromycotrienin II [*The Journal of Biological Chemistry*, 270:25949 (1995) are known. It has been reported that these compounds have antibacterial activities and antitumor activities.

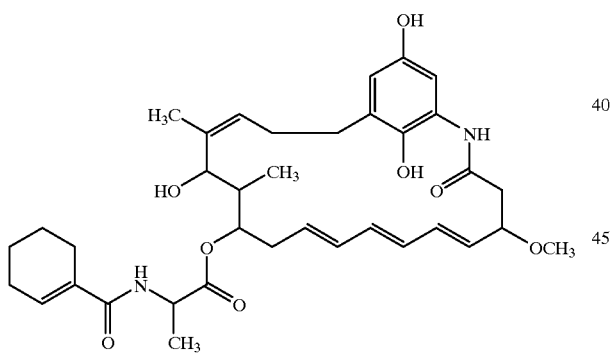

UCF116-B

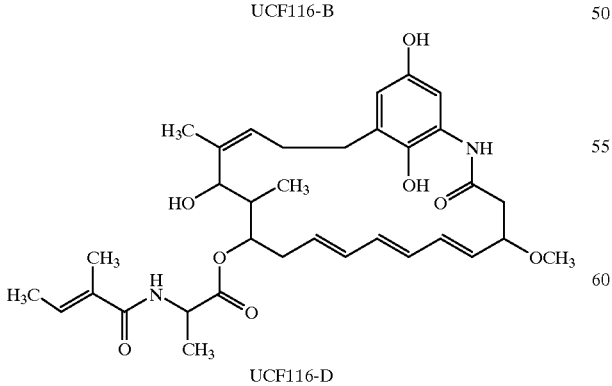

UCF116-D

-continued

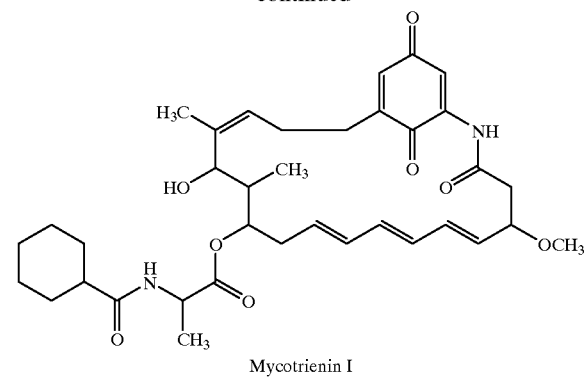

Mycotrienin I

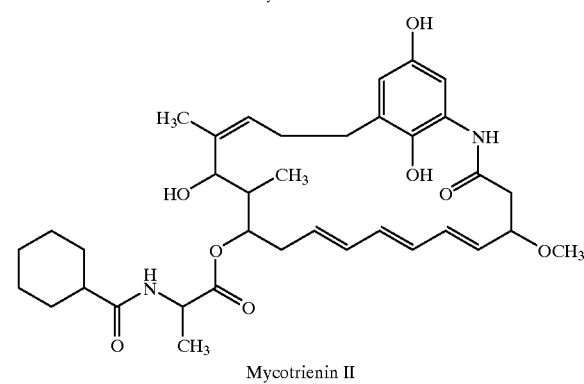

Mycotrienin II

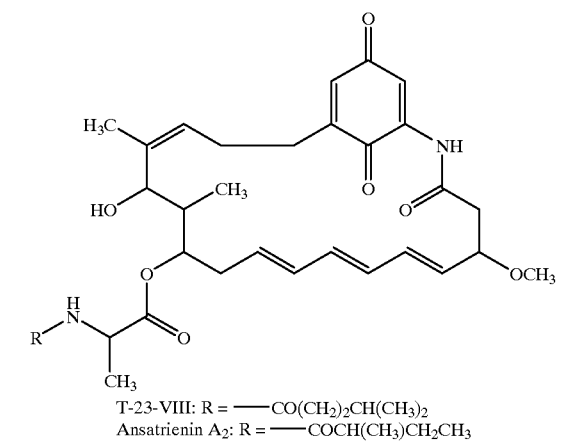

T-23-VIII: R = —CO(CH$_2$)$_2$CH(CH$_3$)$_2$
Ansatrienin A$_2$: R = —COCH(CH$_3$)CH$_2$CH$_3$
Ansatrienin A$_3$: R = —COCH$_2$CH(CH$_3$)$_2$

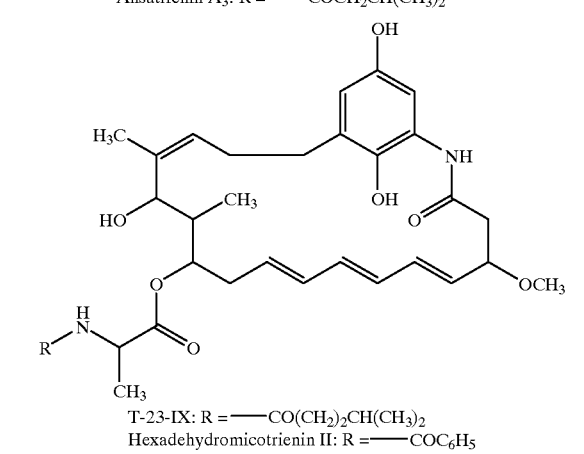

T-23-IX: R = —CO(CH$_2$)$_2$CH(CH$_3$)$_2$
Hexadehydromicotrienin II: R = —COC$_6$H$_5$ -continued

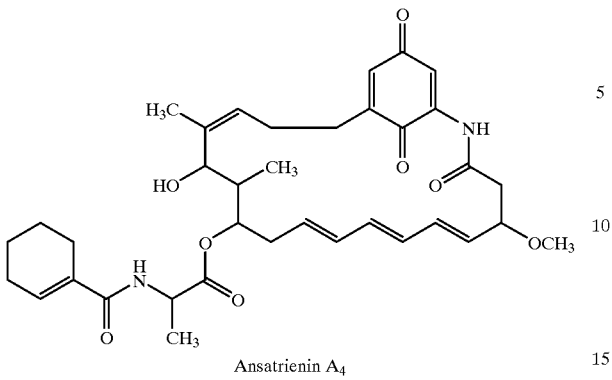

Ansatrienin A₄

Although studies have been widely made on antitumor agents efficacious on solid tumors, there are only few antitumor agents having low toxicity. The present inventors investigated antitumor agents efficacious on solid tumors and, as a result, found that UCF116 derivatives are efficacious on solid tumors while showing low toxicity, thus completing the present invention.

DISCLOSURE OF THE INVENTION

The present invention relates to UCF116 derivatives represented by formula (I):

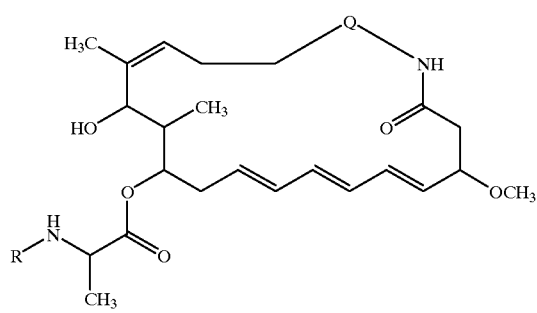

(I)

wherein
Q represents

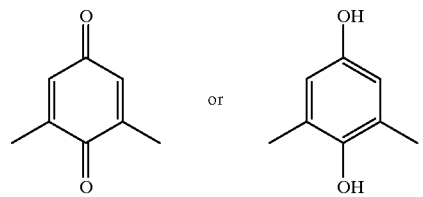

and
R represents
hydrogen,
C(=O)R$^{1a}$ (wherein
R$^{1a}$ represents
methyl,
ethyl,
propyl,
isopropyl,
2,2-dimethylpropyl,
pentyl,
alkyl having 6 to 10 carbon atoms,
1-propenyl,
isopropenyl,
2-methyl-1-propenyl,
substituted or unsubstituted alicyclic alkyl having 3 to 5 carbon atoms,
substituted or unsubstituted aryl,
substituted or unsubstituted aralkyl,
a substituted or unsubstituted heterocyclic group,
substituted or unsubstituted aralkyloxy,
or
substituted lower alkyl),
C(=X)NHR$^{1b}$ (wherein
X represents
an oxygen or sulfur atom, and
R$^{1b}$ represents
substituted or unsubstituted lower alkyl,
substituted or unsubstituted alicyclic alkyl,
substituted or unsubstituted lower alkoxycarbonyl,
substituted or unsubstituted aryl,
substituted or unsubstituted aralkyl, or
a substituted or unsubstituted heterocyclic group), or
SO$_2$R$^{1c}$ (wherein
R$^{1c}$ represents
substituted or unsubstituted lower alkyl,
substituted or unsubstituted aryl,
substituted or unsubstituted aralkyl,
a substituted or unsubstituted heterocyclic group, or
substituted or unsubstituted lower alkenyl),
with the proviso that, when Q is

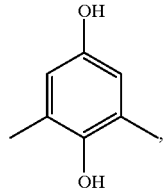

R is not benzoyl,
salts thereof, isomers thereof, hydrates thereof, or solvates thereof.

Furthermore, the present invention relates to a pharmaceutical composition, which comprises the above-described derivative, a pharmaceutically acceptable salt thereof, an isomer thereof, a hydrate thereof or a solvate thereof, and a pharmaceutically acceptable carrier.

Moreover, the present invention relates to an antitumor agent or antibacterial agent, which comprises as an active ingredient the above-described derivative, a pharmaceutically acceptable salt thereof, an isomer thereof, a hydrate thereof or a solvate thereof.

BEST MODE FOR CARRYING OUT THE INVENTION

Hereinafter, the compound represented by formula (I) is referred to as Compound (I). The same shall apply to compounds of other formula numbers.

In the definition of each group in formula (I), examples of the lower alkyl include straight- or branched-chain alkyls having 1 to 10 carbon atoms, such as methyl, ethyl, propyl, isopropyl, butyl, isobutyl, sec-butyl, tert-butyl, pentyl, isopentyl, hexyl, heptyl, octyl, nonyl, and decyl.

Examples of the alkyl having 6 to 10 carbon atoms include those having 6 to 10 carbon atoms among the above-described lower alkyls.

Examples of the alicyclic alkyl include those having 3 to 10 carbon atoms, such as cyclopropyl, cyclobutyl, cyclopentyl, cyclohexyl, cycloheptyl, cyclooctyl, and adamantyl.

Examples of the alicyclic alkyl having 3 to 5 carbon atoms include those having 3 to 5 carbon atoms among the above-described alicyclic alkyls.

A lower alkyl moiety contained in the lower alkoxycarbonyl has the same meaning as the above-described lower alkyl.

Examples of the lower alkenyl include straight- or branched-chain or cyclic alkenyls having 2 to 8 carbon atoms, such as vinyl, allyl, crotyl, 1-propenyl, prenyl, isopropenyl, 2-methyl-2-butenyl, pentenyl, hexenyl, heptenyl, octenyl, cyclobutenyl, cyclopentenyl, and cyclohexenyl.

The aryl is a mono- to tricyclic carbon ring composed of three- to seven-membered rings in which at least one ring is an aromatic ring. Examples include phenyl, naphthyl, anthracenyl, tetrahydronaphthyl, indanyl, and phenanthrenyl.

Examples of the aralkyl include those having 7 to 15 carbon atoms, such as benzyl, phenetyl, benzhydryl, naphthylmethyl, and fluorenylmethyl.

An aralkyl moiety contained in the aralkyloxy has the same meaning as the above-described aralkyl.

The heterocyclic group means a mono- to tricyclic ring composed of three- to eight-membered rings having 1 to 7 carbon atoms and contains at least one of nitrogen, oxygen and sulfur atoms. Examples include heterocyclic groups, such as azepinyl, benzimidazolyl, benzofurazanyl, benzopyranyl, benzothiopyranyl, benzofuryl, benzothiazolyl, benzothiadiazolyl, benzothienyl, benzoxazolyl, chromanyl, cinnolinyl, dihydrobenzofuryl, dihydrobenzothienyl, dihydrobenzothiopyranyl, furyl, imidazolidinyl, imidazolyl, imidazothiazolyl, indolinyl, indolyl, isochromanyl, isoindolyl, isoxazolyl, isoquinolyl, isothiazolyl, isothiazolidinyl, morpholinyl, naphthyridinyl, oxadiazolyl, oxazolyl, 2-oxoazepinyl, 2-oxopiperazinyl, 2-oxopyrrolinyl, 2-oxopyrrolidinyl, piperidinyl, piparazinyl, pyridyl, pyrrazinyl, pyrazolinyl, pyrazolyl, pyrimidinyl, pyrrolidinyl, pyrrolyl, quinazolinyl, quinolinyl, quinoxalinyl, tetrahydrofuryl, tetrahydroisoquinolyl, tetrahydroquinolyl, tetrahydropyranyl, tetrazolyl, thiadiazolyl, thiazolyl, thiazolinyl, thienofuryl, thienothienyl, thienyl, imidazothiazolyl and triazolyl.

A substituent on the lower alkyl, alicyclic alkyl, alicyclic alkyl having 3 to 5 carbon atoms, lower alkenyl, lower alkoxycarbonyl, aryl, aralkyl, aralkyloxy or heterocyclic group is 1 to 3 substituents which are the same or different, such as hydroxy, halogen, nitro, amino, carboxy, cyano, lower alkyl, alicyclic alkyl, lower alkenyl, lower alkoxy, lower alkoxycarbonyl, lower alkanoyl, lower alkylthio, aryl, aryloxy, aryloxy(lower alkyl), lower alkylamino, di(lower alkyl)amino, lower alkanoylamino, aralkyl, aralkyloxy, arylamino, arylsulfonyl, and a heterocyclic group. In the definition of the substituents, the halogen means a fluorine, chlorine, bromine or iodine atom, and the lower alkyl, alicyclic alkyl, lower alkenyl, lower alkoxycarbonyl, aryl, aralkyl, aralkyloxy and heterocyclic group have the same meanings as defined above. Also, the lower alkyl moiety contained in the lower alkoxy, lower alkanoyl, lower alkylthio, lower alkylamino, di(lower alkyl)amino, lower alkanoylamino or aryloxy(lower alkyl) has the same meaning as the above-described lower alkyl. The aryl moiety in the aryloxy, aryloxy (lower alkyl), arylamino and arylsulfonyl has the same meaning as the above-described aryl. Additionally, the substituent may be further substituted with a similar substituent. For example, the alkyl and aryl moieties of the above-described substituent may be substituted with 1 to 3 halogen atoms and the heterocyclic group may be substituted with 1 to 3 substituents such as lower alkyl and trifluoromethyl.

Compound (I) may form a salt, and examples of the salt and pharmaceutically acceptable salt of Compound (I) include an acid addition salt, a metal salt, an ammonium salt, an organic amine addition salt and an amino acid addition salt. Examples of the acid addition salt include an inorganic acid addition salt (e.g., hydrochloride, hydrobromide, sulfate, phosphate, nitrate) and an organic acid addition salt (e.g., formate, acetate, propionate, benzoate, maleate, fumarate, succinate, tartrate, citrate, oxalate, methanesulfonate, p-toluenesulfonate, aspartate, glutamate). Examples of the metal salt include an alkali metal salt (e.g., lithium salt, sodium salt, potassium salt) and an alkaline earth metal salt (e.g., magnesium salt, calcium salt) an aluminum salt, and a zinc salt. Examples of the ammonium salt include ammonium and tetramethylammonium. Examples of the organic amine addition salt include an addition salt of morpholine or piperidine. Examples of the amino acid addition salt include an addition salt of glycine, phenylalanine, glutamic acid, or lysine.

Compound (I) may exist as a various isomer, such as a position isomer, a stereoisomer, an optical isomer, and a tautomer, and all possible isomers and their mixtures of every ratio are also included in the present invention.

Also, Compound (I) and pharmaceutically acceptable salts thereof may exist in the form of an adduct with water or various solvents, and such adducts are also included in the present invention.

Next, methods for the production of Compound (I) are described.

Production Method 1

Among compounds of formula (I), Compound (I) in which Q is

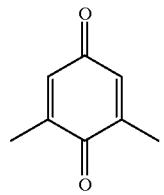

can be produced for example by the following reaction steps.

(Step 1)

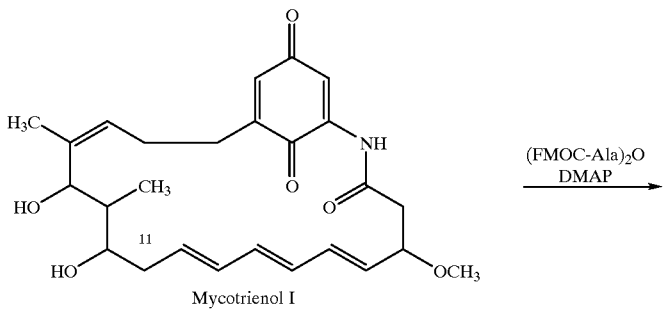
Mycotrienol I

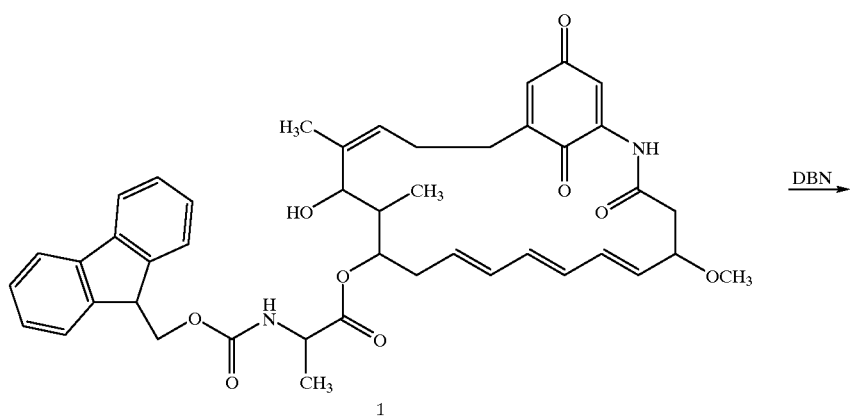
1

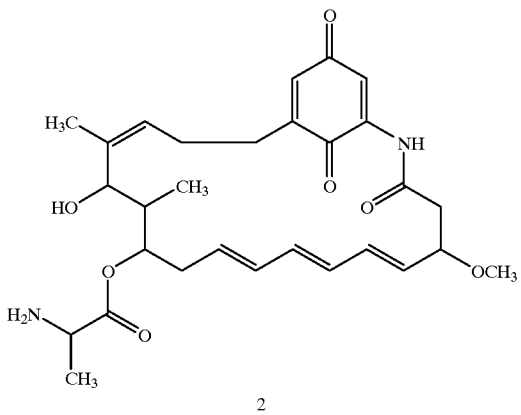
2

(In the above reaction scheme and the following description, FMOC, Ala, DMAP, and DBN represent 9-fluorenylmethoxycarbonyl, alanine, N,N-dimethylaminopyridine, and 1,5-diazabicyclo[4.3.0]non-5-ene, respectively.)

Compound 2 in which $R^1$ in formula (I) is hydrogen can be synthesized from a known compound, mycotrienol I, which can be obtained from UCF116-B or mycotrienin II in accordance with the reported methods [*Tetrahedron Letters*, 23:59 (1982)], *Journal of Antibiotics*, 35:1474 (1982)]. That is, in accordance with the reported method [*Tetrahedron Letters*, 32:1627 (1991)], acid anhydride of D-alanine having an amino group protected with a 9-fluorenylmethoxycarbonyl (FMOC) group is allowed to react with mycotrienol I in the presence of a base, such as dimethylaminopyridine to synthesize Compound 1 in which the alanine residue is selectively introduced into the 11-position hydroxyl group. Compound 2 can be synthesized by removing the FMOC group of the thus obtained Compound 1 in the presence of a base, such as DBN. The protecting group of D-alanine used in this step may be any protecting group usually used in peptide synthesis, so that anhydride of alanine protected with carbobenzoxy, tert-butoxycarbonyl or the like can also be used.

(Step 2)

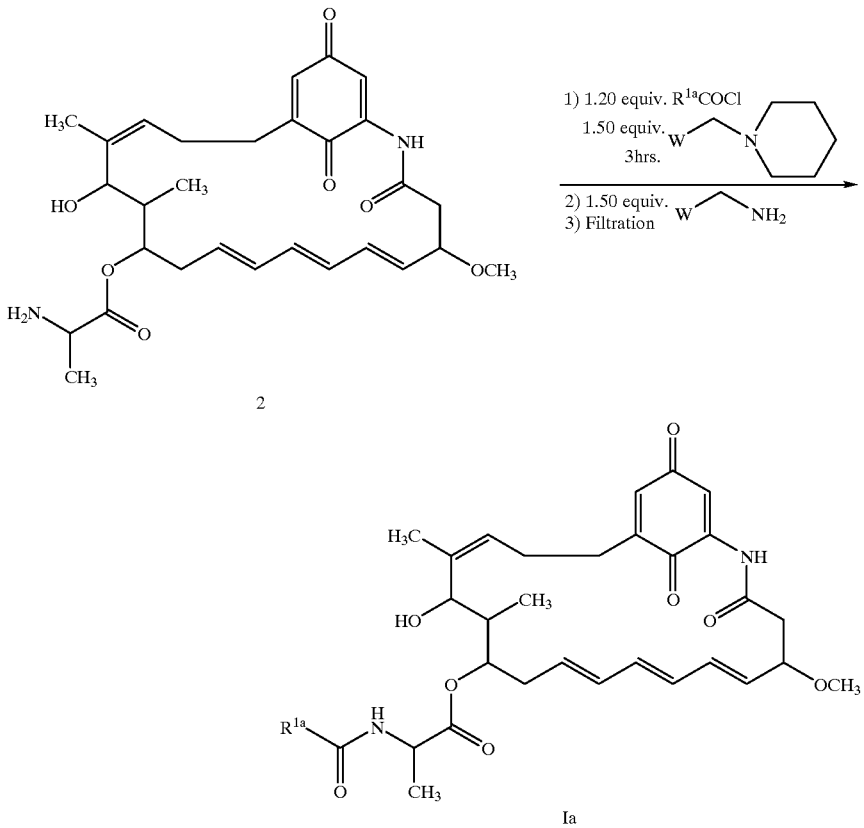

(In the above reaction scheme, R$^{1a}$ has the same meaning as defined above, and W represents an insoluble resin.)

Among compounds of formula (I), Compound Ia in which R is represented by C(=O)R$^{1a}$ can be synthesized by allowing Compound 2 to react with various types of acid chloride (R$^{1a}$COCl) in an inert solvent, such as dichloromethane, in the presence of a basic resin, such as (piperidinomethyl)polystyrene. After completion of the reaction, a basic resin, such as (aminomethyl)polystyrene, is further added thereto to remove excess acid chloride, the resin is removed by filtration and then the solvent is evaporated to obtain Compound Ia with a high purity. In step 2 and the following step 3 or 4, the insoluble resin represented by W means an insoluble resin generally used as a solid phase carrier in the field of combinatorial chemistry, peptide solid phase synthesis and the like, and a cross-linked polystyrene resin is used preferably. The basic solid phase carrier for use in the present invention can be obtained as a commercial item or synthesized in accordance with known methods.

(Step 3)

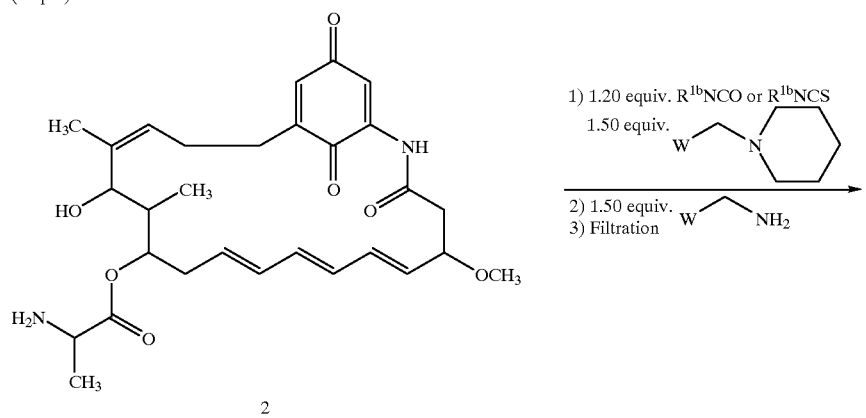

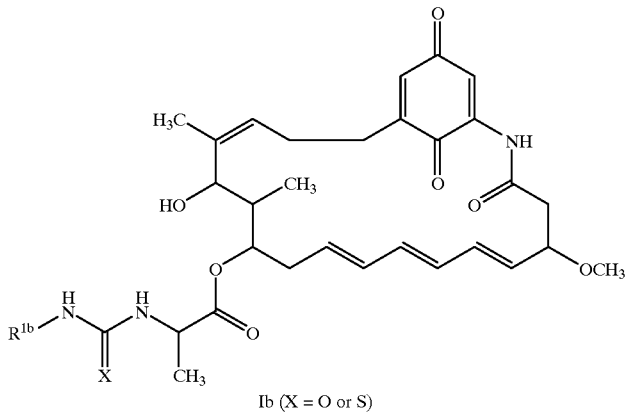

Ib (X = O or S)

(In the above reaction scheme, $R^{1b}$ and X have the same meanings as defined above, and W represents an insoluble resin as defined above.)

Among compounds of formula (I), Compound Ib in which R is $R^{1b}$NHCO or $R^{1b}$NHCS can be synthesized by allowing Compound 2 to react with various types of isocyanate ($R^{1b}$NCO) or isothiocyanate ($R^{1b}$NCS) in an inert solvent, such as dichloromethane, in the presence of a basic resin, such as (piperidinomethyl)polystyrene. After completion of the reaction, a basic resin, such as (aminomethyl) polystyrene, is further added thereto to remove excess isocyanate or isothiocyanate, the resin is removed by filtration and then the solvent is evaporated to obtain Compound Ib with a high purity.

(Step 4)

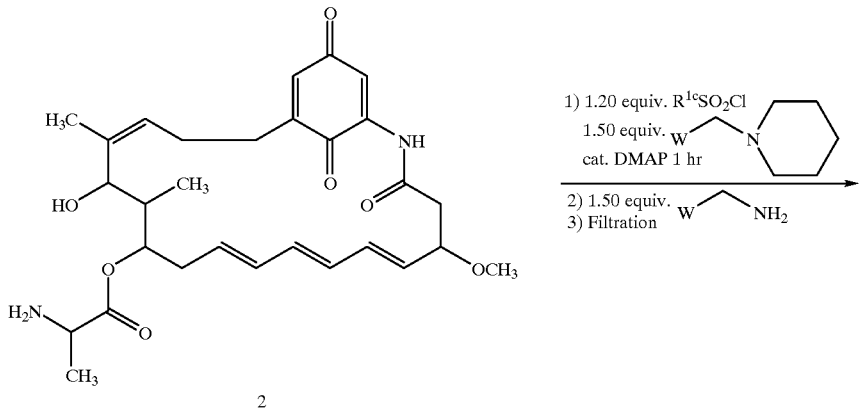

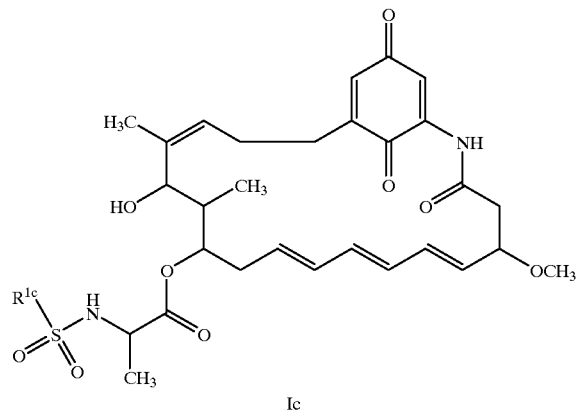

Ic (In the above reaction scheme, $R^{1c}$ has the same meaning as defined above, and W represents an insoluble resin as defined above.)

Among compounds of formula (I), Compound Ic in which R is $R^{1c}SO_2$ can be synthesized by allowing Compound 2 to react with various types of sulfonyl chloride ($R^{1c}SO_2Cl$) in an inert solvent, such as dichloromethane, in the presence of a basic resin, such as (piperidinomethyl)polystyrene. After completion of the reaction, a basic resin, such as (aminomethyl)polystyrene, is further added thereto to remove excess sulfonyl chloride, the resin is removed by filtration and then the solvent is evaporated to obtain Compound Ic with a high purity.

In the above steps 2 to 4, respective compounds of interest can also be obtained using an organic base, such as pyridine, triethylamine, or DMAP, instead of a basic resin, such as (piperidinomethyl)polystyrene or (aminomethyl)polystyrene.

Production Method 2

Compound Ie in which Q of the general formula (I) is represented by

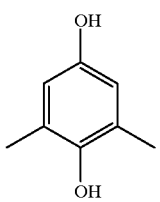

can be obtained from Compound Id in which Q of the general formula (I) is represented by

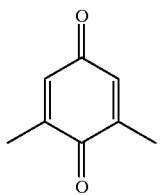

in accordance, for example, with the following step.

(Step 5)

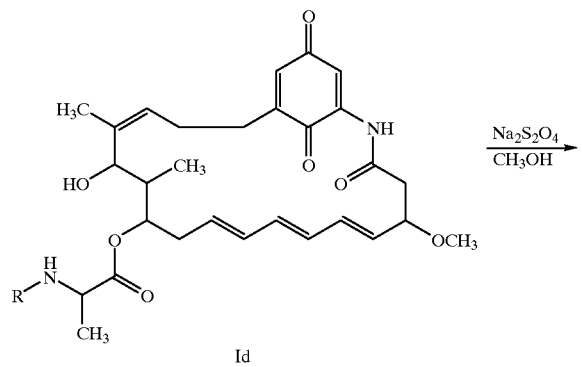

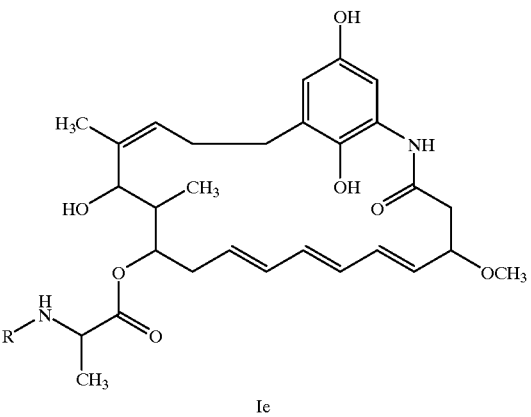

(In the above reaction scheme, R has the same meaning as defined above.)

Compound Ie can be synthesized by treating Compound Id with one equivalent to a large excess of a reducing agent, such as $Na_2S_2O_4$, in a solvent, such as methanol.

In the above steps 1 to 4, the amount of each of the reagents or insoluble resins used is not limited to the equivalent amount described in each reaction scheme, and they can be used in an amount of 1 to 10 equivalent based on the material compound. Also, in the above steps 1 to 5, each reaction is carried out at a temperature of −80 to 60° C.

In addition to the techniques described above, conversion of functional groups in the above-described production methods can also be carried out in accordance with a known method {for example, the method described in *Comprehensive Organic Transformations*, edited by R. C. Larock (1989)}.

Isolation and purification of respective products formed in the above-described production methods can be carried out by employing optional combinations of techniques generally used in the field of organic synthesis, such as filtration, extraction, washing, drying, concentration, crystallization, and various chromatographic means.

Structures and physical properties of typical examples of Compound (I) are shown in Tables 1 to 3.

TABLE 1

Structures and MS spectra of Compound (I) (1)

| Q / R | Compound (2,6-dimethylbenzoquinone) | MS | Compound (2,6-dimethylhydroquinone) | MS |
|---|---|---|---|---|
| H₃C-C(=O)- | 3 | 569 (M + H)⁺ | 123 | 571 (M + H)⁺ |
| cyclopropyl-C(=O)- | 4 | 595 (M + H)⁺ | 124 | 597 (M + H)⁺ |
| cyclopentyl-CH₂CH₂-C(=O)- | 5 | 651 (M + H)⁺ | 125 | 675 (M + Na)⁺ |
| H₃C-(CH₂)₄-C(=O)- | 6 | 625 (M + H)⁺ | 126 | 627 (M + H)⁺ |
| (H₃C)₃C-CH₂-C(=O)- | 7 | 625 (M + H)⁺ | 127 | 627 (M + H)⁺ |
| Ph-C(=O)- | 8 | 631 (M + H)⁺ | | |
| PhO-CH₂-C(=O)- | 9 | 661 (M + H)⁺ | 128 | 663 (M + H)⁺ |
| 4-Cl-C₆H₄-CH₂-C(=O)- | 10 | 679 (M + H)⁺ | 129 | 681 (M + H)⁺ |

TABLE 1-continued

Structures and MS spectra of Compound (I) (1)

(I)

| Q | | | | |
|---|---|---|---|---|
| R | Compound | MS (2,6-dimethylbenzoquinone) | Compound | MS (2,6-dimethylhydroquinone) |
| 1-naphthyl-C(O)- | 11 | 681 (M + H)+ | 130 | 683 (M + H)+ |
| 3,4-dichlorophenyl-C(O)- | 12 | 699 (M + H)+ | 131 | 701 (M + H)+ |
| 4-fluorophenyl-C(O)- | 13 | 649 (M + H)+ | 132 | 651 (M + H)+ |
| 3,5-dimethoxyphenyl-C(O)- | 14 | 691 (M + H)+ | 133 | 693 (M + H)+ |
| 3-fluorophenyl-C(O)- | 15 | 649 (M + H)+ | 134 | 673 (M + Na)+ |

TABLE 1-continued

Structures and MS spectra of Compound (I) (1)

(I)

| Q R | Compound (quinone) | MS | Compound (hydroquinone) | MS |
|---|---|---|---|---|
| 2-Cl-C6H4-C(O)- | 16 | 665 (M + H)+ | 135 | 667 (M + H)+ |
| 3-H3CO-C6H4-C(O)- | 17 | 661 (M + H)+ | 136 | 663 (M + H)+ |
| 4-Cl-C6H4-O-CH2-C(O)- | 18 | 695 (M + H)+ | 137 | 697 (M + H)+ |
| 3-H3C-C6H4-C(O)- | 19 | 645 (M + H)+ | 138 | 647 (M + H)+ |
| 4-(CH3)3C-C6H4-C(O)- | 20 | 687 (M + H)+ | 139 | 711 (M + Na)+ |
| 4-F3CO-C6H4-C(O)- | 21 | 715 (M + H)+ | 140 | 739 (M + Na)+ |

TABLE 1-continued
Structures and MS spectra of Compound (I) (1)
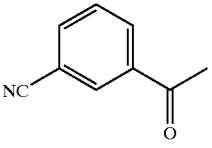
(I)
| Q R | 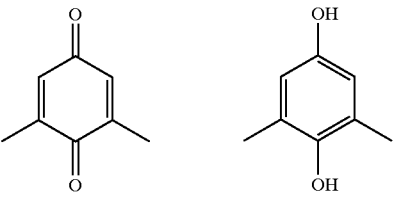 Compound | MS | 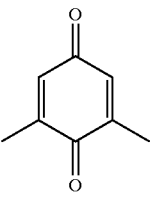 Compound | MS |
|---|---|---|---|---|
| 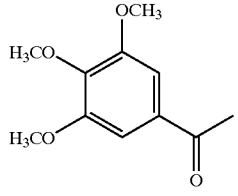 | 22 | 678 (M + Na)+<br>656 (M + H)+ | 141 | 680 (M + Na)+ |
| 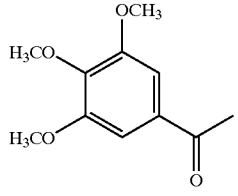 | 23 | 721 (M + H)+ | 142 | 745 (M + Na)+ |
| 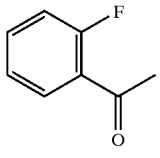 | 24 | 649 (M + H)+ | 143 | 673 (M + Na)+ |
| 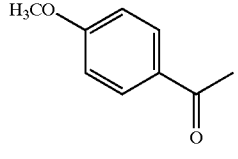 | 25 | 661 (M + H)+ | 144 | 685 (M + Na)+ |
| 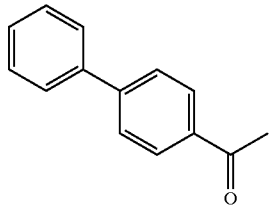 | 26 | 707 (M + H)+ | 145 | 731 (M + Na)+ |

TABLE 1-continued

Structures and MS spectra of Compound (I) (1)

(I)

| Q<br>R | Compound (quinone) | MS | Compound (hydroquinone) | MS |
|---|---|---|---|---|
| Q: 2,6-dimethyl-1,4-benzoquinone; R: 4-chlorophenacyl | 27 | 665 (M + H)⁺ | 146 | 689 (M + Na)⁺ |
| R: 4-chloro-3-nitrophenacyl | 28 | 732 (M + Na)⁺<br>710 (M + H)⁺ | 147 | 734 (M + Na)⁺ |
| R: 4-methylphenacyl | 29 | 645 (M + H)⁺ | 148 | 669 (M + Na)⁺ |
| R: (E)-but-2-enoyl (crotonyl) | 30 | 595 (M + H)⁺ | 149 | 619 (M + Na)⁺ |
| R: methacryloyl | 31 | 595 (M + H)⁺ | 150 | 619 (M + Na)⁺ |
| R: 3-methylbut-2-enoyl (senecioyl) | 32 | 609 (M + H)⁺ | 151 | 633 (M + Na)⁺ |

TABLE 1-continued

Structures and MS spectra of Compound (I) (1)

| Q R | Compound (2,6-dimethyl-1,4-benzoquinone) | MS | Compound (2,6-dimethylhydroquinone) | MS |
|---|---|---|---|---|
| 2-thienylcarbonyl | 33 | 637 (M + H)+ | 152 | 661 (M + Na)+ |
| 2-furylcarbonyl | 34 | 621 (M + H)+ | 153 | 645 (M + Na)+ |
| 1-phenyl-5-propyl-1H-pyrazol-4-ylcarbonyl | 35 | 739 (M + H)+ | 154 | 763 (M + Na)+ |
| 2-thienylacetyl | 36 | 651 (M + H)+ | 155 | 653 (M + H)+ |
| isoxazol-3-ylcarbonyl | 37 | 622 (M + H)+ | 156 | 646 (M + Na)+ |
| 5-methylisoxazol-3-ylcarbonyl | 38 | 636 (M + H)+ | 157 | 660 (M + Na)+ |
| 2-chloropyridin-3-ylcarbonyl | 39 | 666 (M + H)+ | 158 | 690 (M + Na)+ |

TABLE 1-continued
Structures and MS spectra of Compound (I) (1)
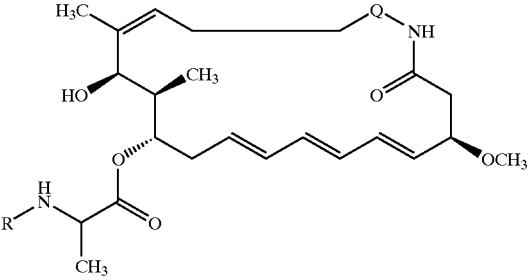
(I)
| | 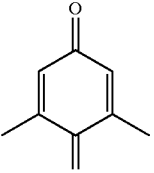 | | 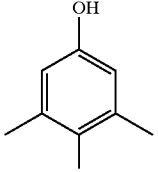 | |
|---|---|---|---|---|
| Q R | Compound | MS | Compound | MS |
| 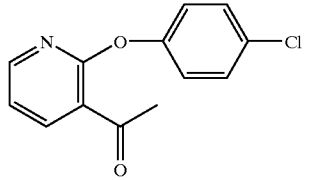 | 40 | 758 (M + H)⁺ | 159 | 782 (M + Na)⁺ |
| 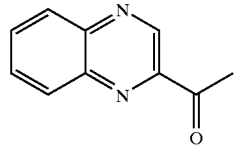 | 41 | 683 (M + H)⁺ | 160 | 707 (M + Na)⁺ |
| 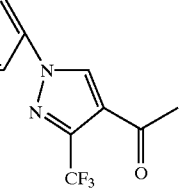 | 42 | 799 (M + H)⁺ | 161 | 823 (M + Na)⁺ |
| 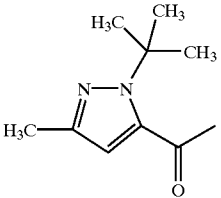 | 43 | 691 (M + H)⁺ | 162 | 693 (M + H)⁺ |
| 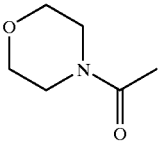 | 44 | 640 (M + H)⁺ | 163 | 664 (M + Na)⁺ |

TABLE 1-continued

Structures and MS spectra of Compound (I) (1)

| R | Q: 2,6-dimethyl-1,4-benzoquinone | | Q: 2,6-dimethylhydroquinone | |
|---|---|---|---|---|
| | Compound | MS | Compound | MS |
| 3-acetyl-2-(methylthio)pyridine | 45 | 678 (M + H)$^+$ | 164 | 680 (M + H)$^+$ |
| 4-acetyl-5-methyl-2-phenyl-2H-1,2,3-triazole | 46 | 712 (M + H)$^+$ | 165 | 736 (M + Na)$^+$ |
| 5-acetyl-1,3-benzodioxole | 47 | 675 (M + H)$^+$ | 166 | 699 (M + Na)$^+$ |
| 5-acetyl-4-methyl-1,2,3-thiadiazole | 48 | 653 (M + H)$^+$ | 167 | 677 (M + Na)$^+$ |
| 1-acetylpyrrolidine | 49 | 624 (M + H)$^+$ | 168 | 648 (M + Na)$^+$ |
| 4-acetyl-3-(2-chlorophenyl)-5-methyl-4,5-dihydroisoxazole | 50 | 746 (M + H)$^+$ | 169 | 770 (M + Na)$^+$ |

TABLE 1-continued
Structures and MS spectra of Compound (I) (1)
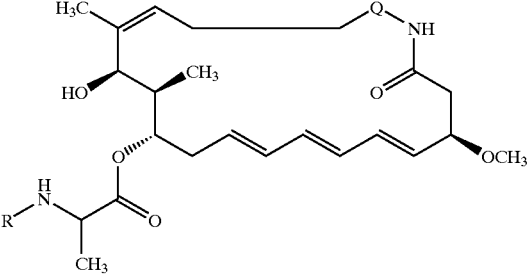
| Q R | Compound | MS | Compound | MS |
|---|---|---|---|---|
| 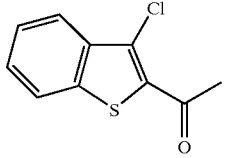 | 51 | 721 (M + H)+ | 170 | 745 (M + Na)+ |
TABLE 2
Structures and MS spectra of Compound (I) (2)
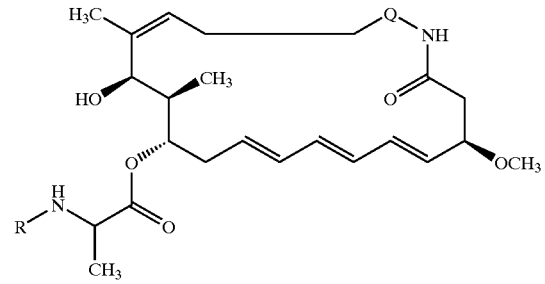
| Q R | Compound | MS | Compound | MS |
|---|---|---|---|---|
| 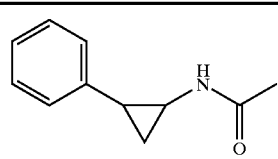 | 52 | 686 (M + H)+ | 171 | 710 (M + Na)+ |

TABLE 2-continued

Structures and MS spectra of Compound (I) (2)

(I)

| R | Q | | | |
|---|---|---|---|---|
| | Compound | MS | Compound | MS |
| 2,4-difluorophenyl-NHC(O)CH₂– | 53 | 682 (M + H)⁺ | 172 | 684 (M + H)⁺ |
| 2-thienyl-CH₂CH₂-NHC(O)CH₂– | 54 | 680 (M + H)⁺ | 173 | 682 (M + H)⁺ |
| 4-methoxyphenyl-NHC(O)CH₂– | 55 | 676 (M + H)⁺ | 174 | 678 (M + H)⁺ |
| 2,4-dichlorophenyl-NHC(O)CH₂– | 56 | 714 (M + H)⁺ | 175 | 716 (M + H)⁺ |
| 4-methoxyphenyl-NHC(S)CH₂– | 57 | 692 (M + H)⁺ | 176 | 694 (M + H)⁺ |
| isopropyl-NHC(O)CH₂– | 58 | 612 (M + H)⁺ | 177 | 614 (M + H)⁺ |
| 4-phenoxyphenyl-NHC(O)CH₂– | 59 | 738 (M + H)⁺ | | |

TABLE 2-continued
Structures and MS spectra of Compound (I) (2)
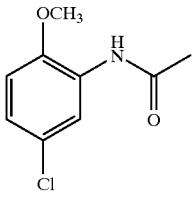
(I)
| | 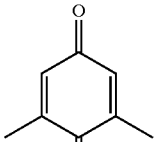 | | 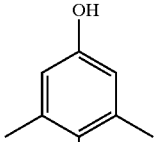 | |
|---|---|---|---|---|
| Q R | Compound | MS | Compound | MS |
| 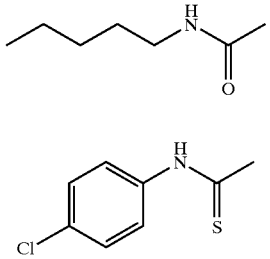 | 60 | 710 (M + H)⁺ | 178 | 712 (M + H)⁺ |
| 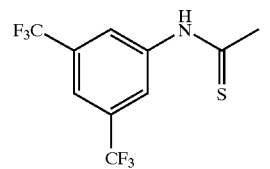 | 61 | 640 (M + H)⁺ | 179 | 642 (M + H)⁺ |
| 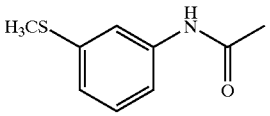 | 62 | 696 (M + H)⁺ | 180 | 698 (M + H)⁺ |
| 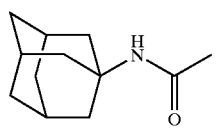 | 63 | 798 (M + H)⁺ | | |
|  | 64 | 692 (M + H)⁺ | 181 | 694 (M + H)⁺ |
|  | 65 | 704 (M + H)⁺ | | |

TABLE 2-continued

Structures and MS spectra of Compound (I) (2)

(I)

| Q R | Compound (Q = 2,6-dimethylbenzoquinone) | MS | Compound (Q = 2,6-dimethylhydroquinone) | MS |
|---|---|---|---|---|
| ethyl 2-acetamido-4-(methylthio)butanoate | 66 | 730 (M + H)+ | 182 | 732 (M + H)+ |
| ethyl 4-acetamidobenzoate | 67 | 718 (M + H)+ | 183 | 720 (M + H)+ |
| ethyl N-(thioacetyl)carbamate | 68 | 658 (M + H)+ | 184 | 682 (M + Na)+ |
| N-(2,5-dimethoxyphenyl)thioacetamide | 69 | 723 (M + 2H)+ | 185 | 725 (M + 2H)+ |
| N-(2,4-dimethoxyphenyl)acetamide | 70 | 706 (M + H)+ | 186 | 708 (M + H)+ |
| N-(2-methoxyphenyl)acetamide | 71 | 676 (M + H)+ | 187 | 678 (M + H)+ |

TABLE 2-continued

Structures and MS spectra of Compound (I) (2)

| Q R | Compound (quinone) | MS | Compound (hydroquinone) | MS |
|---|---|---|---|---|
| 2,4-dichlorophenyl-NH-C(=S)-CH3 | 72 | 730 (M + H)+ | 188 | 732 (M + H)+ |
| 2-biphenyl-NH-C(=O)-CH3 | 73 | 722 (M + H)+ | 189 | 724 (M + H)+ |
| 3-(CF3)phenyl-NH-C(=O)-CH3 | 74 | 714 (M + H)+ | 190 | 716 (M + H)+ |
| 4-chlorophenyl-NH-C(=O)-CH3 | 75 | 680 (M + H)+ | 191 | 682 (M + H)+ |
| cyclohexyl-NH-C(=O)-CH3 | 76 | 652 (M + H)+ | 192 | 654 (M + H)+ |
| 3,5-bis(CF3)phenyl-NH-C(=O)-CH3 | 77 | 782 (M + H)+ | 193 | 784 (M + H)+ |

TABLE 2-continued
Structures and MS spectra of Compound (I) (2)
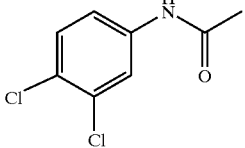
(I)
| Q<br>R | 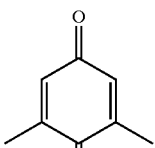<br>Compound | MS | 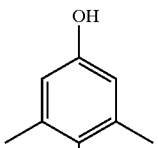<br>Compound | MS |
|---|---|---|---|---|
| 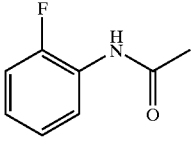 | 78 | 714 (M + H)⁺ | 194 | 716 (M + H)⁺ |
| 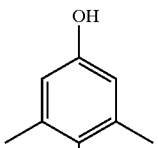 | 79 | 664 (M + H)⁺ | 195 | 666 (M + H)⁺ |
| 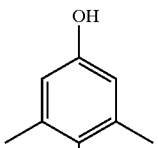 | 80 | 712 (M + H)⁺ | 196 | 714 (M + H)⁺ |
| 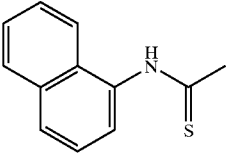 | 81 | 646 (M + H)⁺ | 197 | 648 (M + H)⁺ |
| 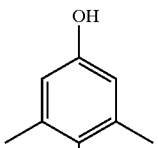 | 82 | 680 (M + H)⁺ | 198 | 682 (M + H)⁺ |
| 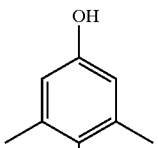 | 83 | 768 (M + H)⁺ | 199 | 770 (M + H)⁺ |

TABLE 2-continued

Structures and MS spectra of Compound (I) (2)

(I)

| Q R | ![quinone] Compound MS | ![hydroquinone] Compound MS |
|---|---|---|
| 4-O₂N-C₆H₄-CH₂-NH-C(O)-CH₃ | 84  691 (M + H)⁺ | |
| C₆H₅-CH₂-NH-C(O)-CH₃ | 85  660 (M + H)⁺ | 200  662 (M + H)⁺ |
| C₆H₅-CH₂-CH₂-NH-C(O)-CH₃ | 86  674 (M + H)⁺ | 201  676 (M + H)⁺ |
| 4-CH₃-C₆H₄-NH-C(O)-CH₃ | 87  660 (M + H)⁺ | 202  662 (M + H)⁺ |
| 4-(Et₂N)-C₆H₄-NH-C(S)-CH₃ | | 203  736 (M + H)⁺ |

TABLE 3

Structures and MS spectra of Compound (I) (3)

| R | Q: quinone (2,6-dimethyl-1,4-benzoquinone) | | Q: hydroquinone (2,6-dimethyl-1,4-hydroquinone) | |
|---|---|---|---|---|
| | Compound | MS | Compound | MS |
| 2-Cl-4-(methylsulfonyl)-acetanilide group | 88 | 758 (M + H)⁺ | 204 | 782 (M + Na)⁺ |
| 2,4-bis(2,2,2-trifluoroethoxy)-3-(methylsulfonyl)phenyl | 89 | 880 (M + NH₄)⁺ | 205 | 887 (M + Na)⁺ |
| methyl 3-methoxy-2-(methylsulfonyl)thiophene-4-carboxylate | 90 | 778 (M + NH₄)⁺ | 206 | 785 (M + Na)⁺ |
| 4-fluorophenyl methylsulfonyl | 91 | 702 (M + NH₄)⁺ | 207 | 709 (M + Na)⁺ |
| phenyl methylsulfonyl | 92 | 684 (M + NH₄)⁺ | 208 | 691 (M + Na)⁺ |

TABLE 3-continued

Structures and MS spectra of Compound (I) (3)

| Q R | Compound | MS | Compound | MS |
|---|---|---|---|---|
| (phenylsulfonyl-thiophene-methylsulfonyl) | 93 | 830 (M + NH₄)⁺ | 209 | 837 (M + Na)⁺ |
| (3,5-bis(trifluoromethyl)phenyl methylsulfonyl) | 94 | 820 (M + NH₄)⁺<br>803 (M + H)⁺ | 210 | 827 (M + Na)⁺ |
| (1-methyl-imidazol-4-yl methylsulfonyl) | 95 | 671 (M + H)⁺ | 211 | 673 (M + H)⁺ |
| (4-chlorophenyl methylsulfonyl) | 96 | 718 (M + NH₄)⁺ | 212 | 725 (M + Na)⁺ |
| (styryl methylsulfonyl) | 97 | 710 (M + NH₄)⁺ | 213 | 717 (M + Na)⁺ |
| (benzothiadiazol-4-yl methylsulfonyl) | 98 | 742 (M + NH₄)⁺ | 214 | 749 (M + Na)⁺ |

TABLE 3-continued
Structures and MS spectra of Compound (I) (3)
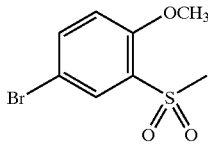
(I)
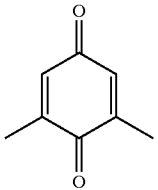 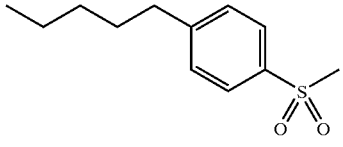
| Q<br>R | Compound | MS | Compound | MS |
|---|---|---|---|---|
| 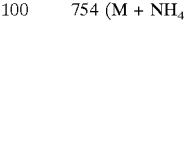 | 99 | 792 (M + NH$_4$)$^+$ | 215 | 799 (M + Na)$^+$ |
| 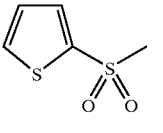 | 100 | 754 (M + NH$_4$)$^+$ | 216 | 761 (M + Na)$^+$ |
| 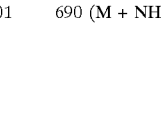 | 101 | 690 (M + NH$_4$)$^+$ | | |
| 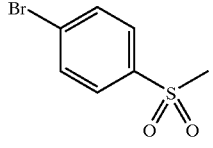 | 102 | 764, 762<br>(M + NH$_4$)$^+$ | 217 | 771, 769<br>(M + Na)$^+$ |
| 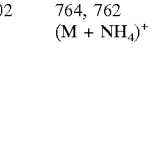 | 103 | 804, 802<br>(M + NH$_4$)$^+$<br>787, 785<br>(M + H)$^+$ | 218 | 811, 809<br>(M + Na)$^+$ |
| 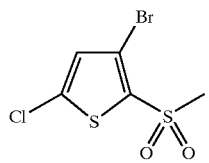 | 104 | 718 (M + NH$_4$)$^+$ | 219 | 725 (M + Na)$^+$ |

TABLE 3-continued

Structures and MS spectra of Compound (I) (3)

(I)

| R | Q | Compound (quinone) | MS | Compound (hydroquinone) | MS |
|---|---|---|---|---|---|
| 2,4,6-trichlorophenyl-SO$_2$- | | 105 | 786 (M + NH$_4$)$^+$ | 220 | 793 (M + Na)$^+$ |
| 2,5-dichlorophenyl-SO$_2$- | | 106 | 752 (M + NH$_4$)$^+$ | 221 | 759 (M + Na)$^+$ |
| 3-fluorophenyl-SO$_2$- | | 107 | 702 (M + NH$_4$)$^+$<br>685 (M + H)$^+$ | 222 | 709 (M + Na)$^+$ |
| quinolin-8-yl-SO$_2$- | | 108 | 718 (M + H)$^+$ | 223 | 720 (M + H)$^+$ |
| 2-(trifluoromethyl)phenyl-SO$_2$- | | 109 | 752 (M + NH$_4$)$^+$ | 224 | 759 (M + Na)$^+$ |
| 4-(acetamido)phenyl-SO$_2$- | | 110 | 741 (M + NH$_4$) | | |

TABLE 3-continued

Structures and MS spectra of Compound (I) (3)

(I)

| | | Q (2,6-dimethyl-1,4-benzoquinone) | | R (2,6-dimethylhydroquinone) | |
|---|---|---|---|---|---|
| Q / R | | Compound | MS | Compound | MS |
| 3-chloro-2-methylphenyl methylsulfonyl | | 111 | 732 (M + NH₄)⁺<br>715 (M + H)⁺ | 225 | 739 (M + Na)⁺ |
| 5-chloro-1,3-dimethyl-4-(methylsulfonyl)pyrazole | | 112 | 736 (M + NH₄)⁺ | 226 | 743 (M + Na)⁺ |
| 1-(methylsulfonyl)naphthalene | | 113 | 734 (M + NH₄)⁺ | 227 | 741 (M + Na)⁺ |
| methylsulfonylmethyl | | 114 | 622 (M + NH₄)⁺ | 228 | 629 (M + Na)⁺ |
| 1-methyl-5-trifluoromethyl-3-[5-(methylsulfonyl)thiophen-2-yl]pyrazole | | 115 | 838 (M + NH₄)⁺<br>821 (M + H)⁺ | 229 | 845 (M + Na)⁺ |
| 6-chloro-5-(methylsulfonyl)imidazo[2,1-b]thiazole | | 116 | 747 (M + H)⁺ | 230 | 749 (M + H)⁺ |

TABLE 3-continued

Structures and MS spectra of Compound (I) (3)

(I)

[Structure of Compound (I) shown with Q and R substituents]

| R | Compound (Q = 2,6-dimethylbenzoquinone) | MS | Compound (Q = 2,6-dimethylhydroquinone) | MS |
|---|---|---|---|---|
| 2-naphthyl-SO₂- | 117 | 734 (M + NH₄)⁺ | 231 | 741 (M + Na)⁺ |
| 2,4,6-trimethylphenyl-SO₂- | 118 | 726 (M + NH₄)⁺ | 232 | 733 (M + Na)⁺ |
| benzofurazan-4-yl-SO₂- | 119 | 726 (M + NH₄)⁺ | 233 | 733 (M + Na)⁺ |
| 4-NC-C₆H₄-SO₂- | 120 | 709 (M + NH₄)⁺ | 234 | 716 (M + Na)⁺ |
| 4-CH₃O-C₆H₄-SO₂- | 121 | 714 (M + NH₄)⁺ | 235 | 721 (M + Na)⁺ |
| (CH₃)₂CH-SO₂- | 122 | 633 (M + H)⁺ | | |

Compound (I) or a pharmaceutically acceptable salt thereof is administered orally or parenterally as it is or as various pharmaceutical compositions. The dosage form of the pharmaceutical compositions includes tablets, pills, powders, granules, capsules, suppositories, injections, and drops.

Preparation of the above dosage forms can be carried out according to conventional methods. For example, the composition may contain various excipients, lubricants, binders, disintegrators, suspending agents, isotonizing agents, emulsifiers, and absorbefacients.

Examples of the carrier used in the pharmaceutical compositions include water, distilled water for injection, physiological saline, glucose, fructose, sucrose, mannitol, lactose, starch, corn starch, cellulose, methyl cellulose, carboxymethyl cellulose, hydroxypropyl cellulose, alginic acid, talc, sodium citrate, calcium carbonate, calcium hydrogen phosphate, magnesium stearate, urea, silicone resin, sorbitan fatty acid ester, and glycerine fatty acid ester. They are appropriately selected according to the kind of the preparation.

The dosage and administration schedule vary depending on the effect of treatment, the administration route, the period of treatment, the age, the body weight, and the like. The compound is usually administered at a dose level of 0.01 mg to 200 mg/kg once or a few times per day for an adult orally or parenterally (for example, injection, drop, intrarectal administration by suppositories, application to skin). Since the dosage depends on various factors as stated above, lower doses may be sufficient, or higher doses may be required.

The solid compositions for oral administration in the present invention include tablets, pills, capsules, powders, and granules.

The solid compositions are prepared by mixing at least one active ingredient with at least one inert diluent, such as lactose, mannitol, glucose, hydroxypropyl cellulose, microcrystalline cellulose, starch, polyvinylpyrrolidone, metasilicate, and magnesium aluminate.

The solid compositions can contain customarily employed additives other than the inert diluent, such as lubricants (e.g., magnesium stearate), disintegrators (e.g., cellulose calcium glycolate), stabilizers (e.g., human serum albumin, lactose), and adjuvants for solubilization and dissolution (e.g., arginine, glutamic acid, aspartic acid).

The tablets or pills, if desired, can be coated with a film of a gastric or enteric substance (e.g., sucrose, gelatin, hydroxypropyl cellulose, hydroxypropylmethyl cellulose phthalate).

The capsules include hard capsules and soft capsules.

The liquid compositions for oral administration include solutions, emulsions, suspensions, syrups, and elixirs.

The liquid compositions for oral administration can contain generally used inert diluents (e.g., purified water).

The liquid compositions can contain adjuvants, such as wetting agents, adjuvants for solubilization and dissolution, suspending agents, sweeteners, flavors, aromatics, and antiseptics in addition to the inert diluents.

Other compositions for oral administration include sprays containing at least one active ingredient, which are prepared in a conventional manner. Sprays can contain stabilizers (e.g., sodium sulfite) and buffers for making the composition isotonic (e.g., sodium chloride, sodium citrate, citric acid) in addition to the inert diluents.

The injectable preparations for parenteral administration include sterile aqueous or nonaqueous solutions, suspension or emulsions.

The injectable preparations are prepared by mixing at least one active ingredient with at least one inert aqueous diluent (e.g., distilled water for injections, physiological saline) or inert nonaqueous diluent (e.g., propylene glycol, polyethylene glycol, plant oil such as olive oil, alcohol such as ethanol, Polysorbate 80 (registered trade name)). They can further contain antiseptics, wetting agents, emulsifiers, dispersants, stabilizers (e.g., human serum albumin, lactose), and adjuvants for solubilization and dissolution.

The resulting liquid compositions are usually sterilized by filtration, incorporation of bactericides or irradiation. The sterilized composition may be solidified by, for example, freeze-drying, to obtain a solid composition, which is dissolved in aseptic water or aseptic diluent for injection on use.

The present invention will now be illustrated in greater detail with reference to Examples, Reference Examples, and Test Examples, but it should be understood that the present invention is not construed as being limited thereto.

EXAMPLE 1

Synthesis of Compound 1

Mycotrienol I (300 mg, 0.68 mmol) was taken up in 40 mL of dry $CH_2Cl_2$ under argon, and DMAP (414 mg, 3.40 mmol) was added thereto and stirred until completely dissolved. The reaction mixture was then cooled to $-78°$ C. upon which $(FMOC-D-Ala)_2O$ (362 mg, 0.60 mmol) was added neat. After stirring the mixture at $-78°$ C. for 8 hours, the reaction mixture was quenched with 10 g of silica gel and gradually warmed to room temperature over a 20 minute period. The mixture was filtered and the silica gel pad was washed with 40:1 $CH_2Cl_2$/methanol until the silica gel was no longer yellow (4×50 mL). The filtrate was concentrated and chromatographed (40:1 $CH_2Cl_2$/methanol, Rf=0.62) to afford 374 mg of Compound 1 as a yellow solid in 75% yield.

HRFAB (high resolution fast atom bombardment mass spectrum) calcd for $C_{44}H_{48}N_2O_9Na$ $(M+Na)^+$ 771.3258, found 771.3229 $^1HNMR$ ($CDCl_3$, 300 MHz) $\delta$ 8.22 (br s, 1H), 7.82–7.25 (m, 10H), 6.46 (br s, 1H), 6.20–5.80 (m, 5H), 5.65–4.80 (m, 5H), 4.65–3.95 (m, 5H), 3.34 (s, 3H), 2.90–1.80 (m, 8H), 1.77 (s, 3H), 1.42 (d, J=7.0 Hz, 3H), 0.85 (d, J=6.8 Hz, 3H).

EXAMPLE 2

Synthesis of Compound 2

Compound 1 (100 mg, 0.14 mmol) was taken up in 50 mL of dry ethyl acetate under argon, and DBN (17 $\mu$L, 0.13 mmol) in 1 mL of ethyl acetate was dropwise added thereto. After stirring at room temperature for 1 hour, the reaction mixture was quickly concentrated and chromatographed (4:1 $CH_2Cl_2$/methanol, Rf=0.46) to afford 36 mg of Compound 2 as a yellow solid in 50% yield.

$^1HNMR$ ($CDCl_3$, 300 MHz) $\delta$ 8.15 (br s, 1H), 7.44 (d, J=2.2 Hz, 1H), 6.43 (d, J=2.2 Hz, 1H), 6.25–5.80 (m, 4H), 5.60–5.40 (m, 2H), 5.28–5.20 (m, 1H), 4.94–4.87 (m, 1H), 4.44 (d, J=4.1 Hz, 1H), 4.05–3.98 (m, 1H), 3.60 (q, J=7.0 Hz, 1H), 3.36 (s, 3H), 2.80 (dd, J=13.0, 3.6 Hz, 1H), 5.28 (dd, J=13.0, 9.6 Hz, 1H), 2.60–1.60 (m, 7H), 1.78 (s, 3H), 1.33 (d, J=7.7 Hz, 3H), 0.92 (d, J=6.8 Hz, 3H). HRFAB (negative mode) calcd for $C_{29}H_{38}N_2O_7$ $(M^-)$ 526.2679, found 526.2683.

EXAMPLE 3

Synthesis of Compounds 3–51

Compound 2 (2.5 mg, 0.0048 mmol) was dissolved in 0.5 mL of dry $CH_2Cl_2$ and added to a single well containing (piperidinomethyl)polystyrene (3.0 mg, 0.0072 mml, Fluka) in an unmodified 96-deep well plate (Beckman, cat.

267006, 1 mL/well) followed by an appropriate acid chloride (0.0058 mmol) in 0.4 mL of dry $CH_2Cl_2$. The wells were immediately capped (Marsh Biochemical Products, cat. #C1000-8) and the plate was rotated for 3 hours upon which the strip caps were removed and to each well was added aminomethylated polystyrene (4.8 mg, 0.0048 mmol, Aldrich). Each well was again capped and the plate was rotated for an additional 1 hour. The plate was removed, the strip caps were peeled off, and the contents of each well were filtered into a dram vial through a pipette stuffed with a plug cotton absorbent to remove the resins followed by a $CH_2Cl_2$ wash (ca. 1 mL). The filtrate was split in half and transferred to another unmodified Beckman plate (one plate to be reduced to Compounds 123–170) and concentrated down to a fine yellow film. This material was then analyzed by TLC and Ms. Average yields were assumed to be 2 mg by random sampling and average purities were assumed to be more than 90% by TLC analysis. Thus, Compounds 3–51 were obtained. For example, the data of Compounds 8 and 40 are shown below.

Compound 8: HRFAB (negative mode) calcd for $C_{36}H_{42}N_2O_8$, (M$^-$) 630.2941, found 630.2972. Compound 40: HRFAB (positive mode) calcd for $C_{41}H_{44}ClN_3O_9Na$ (M+Na)$^+$ 780.2664, found 780.2689. $^1$HNMR (CDCl$_3$, 300 MHz) δ 8.58–8.49 (m, 1H), 8.25–8.18 (m, 2H), 8.05 (br s, 1H), 7.60–7.00 (m, 6H), 6.42 (br s, 1H), 6.20–5.85 (m, 4H), 5.68–5.40 (m, 2H), 5.22–4.50 (m, 4H), 4.03–3.85 (m, 1H), 3.34 (s, 3H), 2.94 (d, J=5.4 Hz, 1H), 2.83 (dd, J=12.7, 3.5 Hz, 1H), 2.65–1.80 (m, 8H), 1.81 (s, 3H), 1.55 (d, J=7.1 Hz, 3H), 0.84 (d, J=7.0 Hz, 3H).

EXAMPLE 4

Synthesis of Compounds 52–87

Compound 2 (2.5 mg, 0.0048 mmol) was dissolved in 0.5 mL of dry $CH_2Cl_2$ and added to a single well containing (piperidinomethyl)polystyrene (3.0 mg, 0.0072 mmol, Fluka) in an unmodified 96-deep well plate (Beckman, cat. #267006, 1 mL/well) followed by an appropriate isothiocyanate or isocyanate (0.0058 mmol) in 0.4 mL of dry $CH_2Cl_2$. The wells were immediately capped (Marsh Biochemical Products, cat. #C1000-8) and the plate was rotated for 6 hours upon which the strip caps were removed and to each well was added aminomethylated polystyrene (4.8 mg, 0.0048 mmol, Aldrich). Each well was again capped and the plate was rotated for an additional 1 hour. The plate was removed, the strip caps were peeled off, and the contents of each well were filtered into a dram vial through a pipette stuffed with a plug cotton absorbent to remove the resins followed by a $CH_2Cl_2$ wash (ca. 1 mL). The filtrate was split in half and transferred to another unmodified Beckman plate (one plate to be reduced to Compounds 171–203) and concentrated down to a fine yellow film. This material was then analyzed by TLC and MS. Average yields were assumed to be 2 mg by random sampling and average purities were assumed to be more than 75% by TLC analysis. Thus, Compounds 52–87 were obtained. For example, the data of Compound 71 are shown below.

Compound 71: HRFAB (positive mode) calcd for $C_{37}H_{45}N_3O_9Na$ (M+Na)$^+$ 698.3054, found 698.3020.

EXAMPLE 5

Synthesis of Compounds 88–122

Compound 2 (2.5 mg, 0.0048 mmol) was dissolved in 0.5 mL of dry $CH_2Cl_2$ with DMAP (6.0 mg, 0.48 mmol) and added to a single well containing (piperidinomethyl)polystyrene (3.0 mg, 0.0072 mml, Fluka) in an unmodified 96-deep well plate (Beckman, cat. #267006, 1 mL/well) followed by an appropriate sulfonylchloride (0.0058 mmol) in 0.4 mL of dry $CH_2Cl_2$. The wells were immediately capped (Marsh Biochemical Products, cat. #C1000-8) and the plate was rotated for 1 hour upon which the strip caps were removed and to each well was added aminomethylated polystyrene (4.8 mg, 0.0048 mmol, Aldrich). Each well was again capped and the plate was rotated for an additional 1 hour. The plate was removed, the strip caps were peeled off, and the contents of each well were filtered into a dram vial through a pipette stuffed with a plug cotton absorbent to remove the resins followed by a $CH_2Cl_2$ wash (ca. 1 mL). The filtrate was split in half and transferred to another unmodified Beckman plate (one plate to be reduced to Compounds 204–235) and concentrated down to a fine yellow film. This material was then analyzed by TLC and MS. Average yields were assumed to be 2 mg by random sampling and average purities were assumed to be more than 85% by TLC analysis. Thus, Compounds 88–122 were obtained. For example, the data of Compound 92 are shown below.

Compound 92: HRFAB (positive mode) calcd for $C_{35}H_{43}N_2O_9S$ (M+H)$^+$ 667.2689, found 667.2706.

EXAMPLE 6

Synthesis of Compounds 123–170

One of the plates containing crude Compounds 3–52 described in Example 3 was concentrated down to a thin film upon which $Na_2S_2O_4$ (ca. 5 mg/well) was added to each well followed by 0.9 mL of methanol. The wells were strip-capped and vortexed for 1 hour upon which the solution in each well turned colorless. The strip caps were removed and the contents of each well were passed through a glass pipette which contained a small pad of silica gel to filter excess $Na_2S_2O_4$. The filtrate was concentrated to give white powdered thin films. This material was then analyzed by TLC and MS. Average yields were assumed to be 2 mg by random sampling and average purities were assumed to be more than 90% by TLC analysis. Thus, Compounds 123–170 were obtained.

EXAMPLE 7

Synthesis of Compounds 171–203

One of the plates containing crude Compounds 52–87 described in Example 4 was concentrated down to a thin film upon which $Na_2S_2O_4$ (ca. 5 mg/well) was added to each well followed by 0.9 mL of Methanol. The wells were strip-capped and vortexed for 1 hour upon which the solution in each well turned colorless. The strip caps were removed and the contents of each well were passed through a glass pipette which contained a small pad of silica gel to filter excess $Na_2S_2O_4$. The filtrate was concentrated to give white powdered thin films. This material was then analyzed by TLC and MS. Average yields were assumed to be 2 mg by random sampling and average purities were assumed to be more than 75% by TLC analysis. Thus, Compounds 171–203 were obtained.

EXAMPLE 8

Synthesis of Compounds 204–235

One of the plates containing crude Compounds 88–122 described in Example 5 was concentrated down to a thin film upon which $Na_2S_2O_4$ (ca. 5 mg/well) was added to each well followed by 0.9 mL of methanol. The wells were strip-capped and vortexed for 1 hour upon which the solution in each well turned colorless. The strip caps were removed and the contents of each well were passed through a glass pipette which contained a small pad of silica gel to filter excess $Na_2S_2O_4$. The filtrate was concentrated to give white powdered thin films. This material was then analyzed by TLC and MS. Average yields were assumed to be 2 mg by random sampling and average purities were assumed to be 80% by TLC analysis. Thus, Compounds 204–235 were obtained.

REFERENCE EXAMPLE 1

Synthesis of Mycotrienol I

Mycotrienin II (1.00 g, 1.56 mmol) was reduced with $NaBH_4$ as described by the literature method to afford 1.04 g of a crude material. The crude material was immediately oxidized with $FeCl_3$ as described by the literature method to afford 600 mg of Mycotrienol I as a yellow solid after chromatography (25:1 $CH_2Cl_2$/methanol, Rf=0.44) in 87% combined yield.

HRFAB (negative mode) calcd for $C_{24}H_{33}NO_6$ (M$^-$) 455.2308, found 455.2325. $^1$HNMR (CDCl$_3$, 300 MHz) δ 8.06 (br s, 1H), 7.44 (d, J=2.5 Hz, 1H), 6.45 (m, 1H), 6.20–5.45 (m, 7H), 5.18 (t, J=6.8 Hz, 1H), 4.85 (br s, 1H), 4.02–3.60 (m, 2H), 3.34 (s, 3H), 2.79 (dd, J=12.8, 3.5 Hz, 1H), 2.61–1.98 (m, 8H), 1.79 (s, 3H), 0.93 (d, J=7.0 Hz, 3H).

Next, pharmacological activities of Compound (I) are described with reference to test examples.

TEST EXAMPLE 1

Proliferation Inhibition Test on Cells of a Transformant KNRK Obtained by Transforming Cells of a Rat Kidney Epithelial Cell Line NRK with Human K-ras$^{G12V}$ Gene KNRK cells adjusted to a density of $1\times10^5$ cells/ml were dispensed in 1 ml/well portions into a 24 well plate (Nunc #143892) and cultured at 37° C. for 8 hours in a 5% carbon dioxide gas incubator using Dulbecco's modified Eagle's medium (DMEM) containing 10% fetal calf serum (FCS). A DMSO solution of each test compound adjusted to 10 mM was serially diluted with DMEM and dispensed in 0.1 ml portions into the wells and then the culturing was continued for 40 hours. After removing the medium by suction, the thus recovered cells were washed with 0.5 ml of physiological saline and separated using 1 ml of a solution containing 0.125% trypsin and 0.01% EDTA, and a 0.5 ml portion of the resulting cell suspension was diluted with 10 ml of Cell Pack (Toa Medical Electric) and applied to an automatic hemocytometer (F-300, Toa Medical Electric) to count the number of cells and calculate the 50% growth inhibition concentration which was expressed by IC$_{50}$. The results are shown in Table 4.

TABLE 4

Proliferation inhibition test on cells of a transformant KNRK obtained by transforming cells of a rat kidney epithelial cell line NRK with human K-ras$^{B12V}$ gene

| Compound | IC$_{50}$ (µM) |
| --- | --- |
| 8 | 3.6 |
| 15 | 7.8 |
| 40 | 0.84 |
| 50 | 3.9 |
| 53 | 1.5 |
| 55 | 2.2 |
| 57 | 13.3 |
| 62 | 14.2 |
| 64 | 3.0 |
| 71 | 0.3 |
| 79 | 1.5 |
| 80 | 3.0 |
| 81 | 2.0 |
| 82 | 6.4 |
| 87 | 2.3 |
| 97 | 11.5 |
| 134 | 4.7 |
| 169 | 5.2 |
| 197 | 16.3 |
| 213 | 8.7 |

TEST EXAMPLE 2

Antitumor Test on Nude Mouse-transplanted Human Colonic Cancer HCT 116 Solid Tumor Human colonic cancer HCT 116 was abdominal-subcutaneously transplanted into nude mice (female, CD-1 nu/nu mice) and then, by arbitrarily dividing the mice into groups of 5 animals per group on the 7th day after the transplantation, a test compound dissolved in emulphor/PBS was intraperitoneally administered into each mouse once a day for 10 days to measure the tumor weight on the 14th day after commencement of the drug administration. Antitumor activity of the test compound was expressed by the ratio (T/C) of the tumor volume (T) of the test drug-administered group to the tumor volume (C) of the drug-non-administered group on the 14th day after the administration. The results are shown in Table 5.

TABLE 5

Antitumor test on nude mouse-transplanted human colonic cancer HCT 116 solid tumor

| Compound | Dose | T/C (%) |
| --- | --- | --- |
| 71 | 5 mg/kg × 10 | 40 |

While the invention has been described in detail and with reference to specific embodiments thereof, it will be apparent to one skilled in the art that various changes and modifications can be made therein without departing from the spirit and scope thereof.

What is claimed is:

1. A compound represented by formula (I):

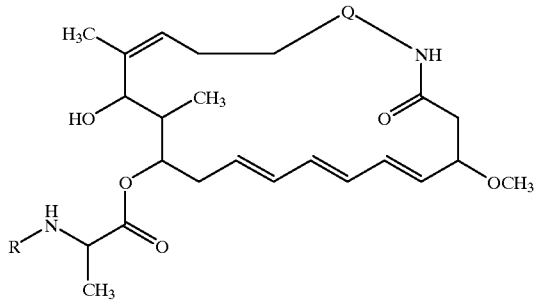

(1)

wherein Q represents

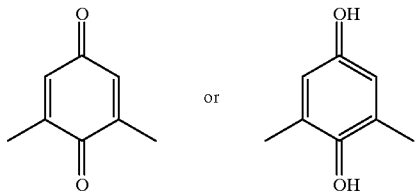

or and R represents hydrogen, C(=O)R$^{1a}$, C(=X)NHR$^{1b}$, or SO$_2$R$^{1c}$ wherein R$^{1a}$ is selected from the group consisting of methyl, ethyl, propyl, isopropyl, 2,2-dimethylpropyl, pentyl, C6–10 alkyl, 1-propenyl, isopropenyl, 2-methyl-1-propenyl, substituted or unsubstituted C3–5 alicyclic alkyl, substituted or unsubstituted aryl, substituted or unsubstituted aralkyl, a substituted or unsubstituted heterocyclic group, substituted or unsubstituted aralkyloxy, and lower alkyl substituted with 1 to 3 substituents independently selected from the group consisting of hydroxy, halogen, nitro, amino, carboxy, cyano, alicyclic alkyl, lower alkenyl, lower alkoxy, lower alkoxycarbonyl, lower alkanoyl, lower alkylthio, aryl, aryloxy, aryloxy(lower alkyl), lower alkylamino, di(lower alkyl)amino, lower alkanoylamino, aralkyl, aralkyloxy, arylamino, arylsulfonyl, and a heterocyclic group, X represents an oxygen or sulfur atom, and R$^{1b}$ represents substituted or unsubstituted lower alkyl, substituted or unsubstituted alicyclic alkyl, substituted or unsubstituted lower alkoxycarbonyl, substituted or unsubstituted aryl, substituted or unsubstituted aralkyl, or a substituted or unsubstituted heterocyclic group, R$^{1c}$ represents substituted or unsubstituted lower alkyl, substituted or unsubstituted aryl, substituted or unsubstituted aralkyl, a substituted or unsubstituted heterocyclic group, or substituted or unsubstituted lower alkenyl, with the proviso that, when Q is

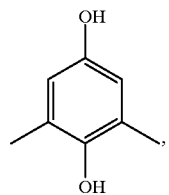

R is not benzoyl,
a salt thereof, an isomer thereof, or a solvate thereof and wherein the substituent on the substituted lower alkyl, substituted alicyclic alkyl, substituted C3–5 alicyclic alkyl, substituted lower alkenyl, substituted lower alkoxycarbonyl, substituted aryl, substituted aralkyl, substituted aralkyloxy and a substituted heterocyclic group is 1 to 3 substituents independently selected from the group consisting of hydroxy, halogen, nitro, amino, carboxy, cyano, lower alkyl, alicyclic alkyl, lower alkenyl, lower alkoxy, lower alkoxycarbonyl, lower alkanoyl, lower alkylthio, aryl, aryloxy, aryloxy(lower alkyl), lower alkylamino, di(lower alkyl)amino, lower alkanoylamino, aralkyl, aralkyloxy, arylamino, arylsulfonyl, and a heterocyclic group, and wherein the heterocyclic group is a mono- to tricyclic ring comprising three- to eight-membered rings having 1 to 7 carbon atoms and at least one nitrogen, oxygen or sulfur atom.

2. The compound according to claim 1, wherein the substituent on the substituted lower alkyl, substituted alicyclic alkyl, substituted C3–5 alicyclic alkyl, substituted lower alkenyl, substituted lower alkoxycarbonyl, substituted aryl, substituted aralkyl, substituted aralkyloxy or substituted heterocyclic group is 1 to 3 substituents independently selected from the group consisting of alicyclic alkyl, lower alkenyl, lower alkoxy, lower alkoxycarbonyl, lower alkanoyl, lower alkylthio, aryl, aryloxy, aryloxy(lower alkyl), lower alkylamino, di(lower alkyl)amino, lower alkanoylamino, aralkyl, aralkyloxy, arylamino, arylsulfonyl, and a heterocyclic group, a salt thereof, an isomer thereof, or a solvate thereof.

3. The compound according to claim 1, wherein R is C(=O)R$^{1a}$ (wherein R$^{1a}$ is methyl; ethyl; propyl; isopropyl; 2,2-dimethylpropyl; pentyl; C6–10 alkyl; 1-propenyl; isopropenyl; 2-methyl-1-propenyl; cyclopropyl; cyclobutyl; cyclopentyl; substituted or unsubstituted aryl; substituted or unsubstituted aralkyl; a substituted or unsubstituted heterocyclic group; substituted or unsubstituted aralkyloxy; or lower alkyl substituted with a substituted or unsubstituted heterocyclic group, alicyclic alkyl or substituted or unsubstituted aryloxy), a salt thereof, an isomer thereof, or a solvate thereof.

4. The compound according to claim 1, wherein R is C(=X)NHR$^{1b}$ (wherein X is an oxygen or sulfur atom, and R$^{1b}$ represents substituted or unsubstituted lower alkyl, substituted or unsubstituted alicyclic alkyl, substituted or unsubstituted lower alkoxycarbonyl, substituted or unsubstituted aryl, substituted or unsubstituted aralkyl, or a substituted or unsubstituted heterocyclic group), a salt thereof, an isomer thereof, or a solvate thereof.

5. The compound according to claim 1, wherein R is SO$_2$R$^{1c}$ (wherein R$^{1c}$ is lower alkyl, substituted or unsubstituted aryl, substituted or unsubstituted aralkyl, a substituted or unsubstituted heterocyclic group, or substituted or unsubstituted lower alkenyl), a salt thereof, an isomer thereof, or a solvate thereof.

6. The compound according to claim 3, wherein $R^{1a}$ is substituted aryl; a substituted or unsubstituted heterocyclic group; substituted or unsubstituted aralkyloxy; or lower alkyl substituted with a substituted or unsubstituted heterocyclic group, alicyclic alkyl or substituted or unsubstituted aryloxy, a salt thereof, an isomer thereof, or a solvate thereof.

7. The compound according to claim 6, wherein $R^{1a}$ is a substituted or unsubstituted heterocyclic group, a salt thereof, an isomer thereof, or a solvate thereof.

8. The compound according to claim 4, wherein $R^{1b}$ is a substituted or unsubstituted heterocyclic group, a salt thereof, an isomer thereof, or a solvate thereof.

9. A pharmaceutical composition, which comprises the compound according to any one of claims 1 to 8, a pharmaceutically acceptable salt thereof, an isomer thereof, or a solvate thereof, and a pharmaceutically acceptable carrier.

10. A method for antibacterial treatment, which comprises selecting a compound according to any one of claims 1 to 8, a pharmaceutically acceptable salt thereof, an isomer thereof, or a solvate thereof and administering said compound to a patient in need thereof.

11. A process of preparing the pharmaceutical composition according to claim 9, a pharmaceutically acceptable salt thereof, an isomer thereof, or a solvate thereof, comprising:

selecting said compound and admixing said compound with said pharmaceutically acceptable carrier.

12. A method for treating colon cancer, which comprises administering an effective amount of the derivative according to any one of claims 1 to 8, a pharmaceutically acceptable salt thereof, an isomer thereof, or a solvate thereof to a patient in need thereof.

* * * * *